United States Patent [19]

Romero-Sierra et al.

[11] 4,248,734

[45] Feb. 3, 1981

[54] PRESERVATION OF DOUGLAS FIR NEEDLES

[75] Inventors: Cesar Romero-Sierra, Bath; John C. Webb, Kingston, both of Canada

[73] Assignee: Queen's University at Kingston, Kingston, Canada

[21] Appl. No.: 112,147

[22] Filed: Jan. 14, 1980

[30] Foreign Application Priority Data

Jan. 30, 1979 [CA] Canada .................................. 320466

[51] Int. Cl.$^3$ .............................................. A01H 1/00
[52] U.S. Cl. .................................... 252/400 R; 71/68; 427/4; 47/DIG. 2; 428/13; 428/22
[58] Field of Search .............................. 71/68; 427/4; 252/400 R, 400 A; 47/DIG. 2; 428/22, 13

[56] References Cited

U.S. PATENT DOCUMENTS 2,567,929  9/1951  Fessenden ................................ 427/4

Primary Examiner—Sam Silverberg

Attorney, Agent, or Firm—Richard J. Hicks; Stanley E. Johnson

[57] ABSTRACT

A solution and process for preserving Douglas Fir needles while preventing shedding thereof from the branch to which they are naturally attached, producing a natural looking product suitable for display purposes. The branches, with attached needles, are immersed in a solution comprising (in amounts per liter of solution):

300–500 ml water
200–300 ml ethyl alcohol
0–75 ml ethylene glycol
50–75 ml propionic acid
0–20 ml glycerin
100–150 ml formalin
50–175 ml propylene glycol
40–75 gms citric acid
1–7 gms magnesium sulphate
15–25 gms cupric sulphate
5–10 gms sodium sulphite
0–10 gms seaweed extract, for a period of up to about two weeks and subsequently air dried.

4 Claims, No Drawings

PRESERVATION OF DOUGLAS FIR NEEDLES

This application is related to our prior U.S. application Ser. No. 061,688 filed July 30, 1979, "Preservation of Green Plant Tissues". This application relates to the preservation of the green needles of certain coniferous trees and in particular to the prevention of needle casting of Douglas Fir.

In our aforesaid earlier application we have described a process for preserving green coloured plant tissues, including pine and spruce needles, in which the tissues are immersed in a solution comprising water, an exchange medium comprising at least one monohydric alcohol, at least one preservative component selected from the group comprising lower carboxylic acids, di- and tri-hydric alcohols and formalin and sufficient buffering, modifying and mordant reagents to control the pH and osmolality of the solution, and then dried. The preservative components of the solution serve three functions: (a) as a biological preservative; (b) as an environmental fixer; and (c) as a biological fixer. Biological preservatives include the lower carboxylic acids, environmental fixers to give "body" to the preserved tissues and provide resistance to weathering include the di- and tri-hydric alcohols, and biological fixers include formalin. We have found that solutions according to our prior application are efficacious for retaining the green colour in most green tissues, including coniferous tree needles. We have now found, however, that although efficacious for colour preservation of individual Douglas Fir needles, there is a problem in that the needles tend to be cast from the branch to which they are attached so that the treated branches have considerably diminished value for display or museum purposes. Without wishing to be bound by this explanation, it is believed that this phenomena, which is believed unique to Douglas Fir, is caused by a lack of resin in the needles which makes the needles particularly susceptible to dehydration rather than exchanging, in the presence of the monohydric alcohol of the treating solution, causing the needle to shrink away from the abscission periderm layer, which forms a strongly defined region between the needle itself and the branch, leaving only the central vascular bundle, which is continuous with the branch, to support the weight of the needle. The vascular bundle is relatively brittle and is easily fractured mechanically thus allowing the needle to drop.

It is an object, therefore, of the present invention to provide a process and a solution for treating Douglas Fir needles which will not only preserve the natural green coloration thereof but also at least substantially prevent needle casting.

By one aspect of this invention there is provided a solution, for the preservation of naturally coloured needles or branches of Douglas Fir substantially without shedding therefrom, consisting essentially of (in amounts per liter):
- 300-500 ml water
- 200-300 ml ethyl alcohol
- 0-75 ml ethylene glycol
- 50-75 ml propionic acid
- 0-20 ml glycerin
- 100-150 ml formalin
- 50-175 ml propylene glycol
- 40-75 gms citric acid
- 1-7 gms magnesium sulphate
- 15-25 gms cupric sulphate
- 5-10 gms sodium sulphite
- 0-10 gms seaweed extract.

By another aspect of this invention there is provided a process for preserving branches of Douglas Fir having naturally green coloured needles thereon substantially without shedding said needles, comprising immersing said needles and branches in a solution comprising:
- 300-500 ml water
- 200-300 ml ethyl alcohol
- 0-75 ml ethylene glycol
- 50-75 ml propionic acid
- 0-20 ml glycerin
- 100-150 ml formalin
- 50-175 ml propylene glycol
- 40-75 gms citric acid
- 1-7 gms magnesium sulphate
- 15-25 gms cupric sulphate
- 5-10 gms sodium sulphite
- 0-10 gms seaweed extract, for a sufficient time to effect exchange of water naturally contained in said needles with said solution, thereby biologically preserving and fixing said natural green colour in said needles and maintaining a bond between said needles and said branches.

As discussed above, it is believed that the casting of Douglas Fir needles is caused by dehydration of the abscission layer of the periderm cells and mechanical breakage of the central vascular bundle and in order to overcome the casting problem we have found that the treatment solution which is employed as in our prior application must be modified in certain particulars so as to strengthen the central vascular bundle and so in turn prevent mechanical breakage thereof while, at the same time, minimizing the dehydration effects of the monohydric alcohols employed. We have specifically found that a relatively large volume (of the order of 10% or more) of formalin is effective to biologically fix or mechanically strengthen the central vascular bundle and that propylene glycol, in amounts considerbly in excess of those suggested in our aforesaid copending application, is particularly suitable as an environmental fixer to exchange with the water held in the cells of the needles without causing either swelling or shrinkage thereof, thus minimizing the dehydrating effects of the monohydric alcohols. The presence of relatively large volumes of formalin, however, has a deleterious browning effect upon the colour of the treated needles and it is therefore also necessary to modify the amounts of the colour enhancers or modifiers in the composition to compensate for this. We have found that cupric sulphate is particularly effective for this purpose. Other minor ingredients have also been found beneficial and may be added as required. In particular we have found that a few grams (of the order of 5-10 gms) of commercially available powdered seaweed extract is beneficial as a colour intensifier and as a bond strengthener.

Particularly preferred treatment solutions comprise (in amounts per liter of solution):
- 300-500 ml water
- 200-300 ml ethyl alcohol (comercial 95% unmatured)
- 0-75 ml ethylene glycol
- 50-75 ml propionic acid
- 0-20 ml glycerin
- 100-150 ml formalin
- 50-175 ml propylene glycol
- 40-70 gms citric acid
- 1-7 gms magnesium sulphate 15-25 gms cupric sulphate
5-10 gms sodium sulphite
0-10 gms seaweed extract.

It will be appreciated that propylene glycol is the preferred environmental fixative in this application, although at least some ethylene glycol is generally employed. As the proportion of ethylene glycol is reduced so the proportion of propylene glycol is increased and can be used as a total replacement.

EXAMPLE 1

Douglas Fir branches, with needles attached, were immersed, at room temperature in a bath containing:

5640 ml distilled water
3840 ml unmatured alcohol
720 ml ethylene glycol
960 ml propionic acid
240 ml glycerin
1800 ml formalin
1100 ml propylene glycol
720 gms citric acid
48 gms magnesium sulphate
250 gms cupric sulphate
96 gms sodium sulphite
50 gms powdered seaweed extract, for a period of two weeks following which the treated specimens were air dried and stored. The needles were of a good green colour and sufficiently firmly attached to the branches to withstand considerable mechanical abuse such as by shaking or impacting on a flat surface, and were therefore suitable for use in a museum display.

We claim:

1. A solution, for the preservation of naturally coloured needles or branches of Douglas Fir substantially without shedding therefrom, consisting essentially of (in amounts per liter):

300-500 ml water
   200-300 ml ethyl alcohol
   0-75 ml ethylene glycol
   50-175 ml propylene glycol
   0-20 ml glycerin
   100-150 ml formalin
   50-175 ml propylene glycol
   40-75 gms citric acid
   1-7 gms magnesium sulphate
   15-25 gms cupric sulphate
   5-10 gms sodium sulphite
   0-10 gms seaweed extract.

2. A solution as claimed in claim 1 consisting of:

394 ml water
   268 ml ethyl alcohol
   50 ml ethylene glycol
   67 ml propionic acid
   17 ml glycerin
   126 ml formalin
   77 ml propylene glycol
   50.3 gms citric acid
   3.3 gms magnesium sulphate
   17.5 gms cupric sulphate
   6.7 gms sodium sulphite
   5 gms seaweed extract.

3. a process for preserving branches of Douglas Fir having naturally green coloured needles thereon substantially without shedding said needles comprising immersing said needles and branches in a solution comprising:

300-500 ml water
   200-300 ml ethyl alcohol
   0-75 ml ethylene glycol
   50-75 ml propionic acid
   0-20 ml glycerin
   100-150 ml formalin
   50-175 ml propylene glycol
   40-75 gms citric acid
   1-7 gms magnesium sulphate
   15-25 gms cupric sulphate
   5-10 gms sodium sulphite
   0-10 gms seaweed extract. for a sufficient time to effect exchange of water naturally contained in said needles with said solution, thereby biologically preserving and fixing said natural green colour in said needles and maintaining a bond between said needles and said branches.

4. A process as claimed in claim 3 wherein said solution comprises:

394 ml water
   268 ml ethyl alcohol
   50 ml ethylene glycol
   67 ml propionic acid
   17 ml glycerin
   126 ml formalin
   77 ml propylene glycol
   50.3 gms citric acid
   3.3 gms magnesium sulphate
   17.5 gms cupric sulphate
   6.7 gms sodium sulphite
   5 gms seaweed extract.

* * * * *